United States Patent [19]

Ayer et al.

[11] Patent Number: 4,624,847

[45] Date of Patent: Nov. 25, 1986

[54] DRUG DELIVERY DEVICE FOR PROGRAMMED DELIVERY OF BENEFICIAL DRUG

[75] Inventors: Atul D. Ayer, Mt. View; Brian Barclay, Sunnyvale, both of Calif.

[73] Assignee: ALZA Corporation, Palo Alto, Calif.

[21] Appl. No.: 725,839

[22] Filed: Apr. 22, 1985

[51] Int. Cl.$^4$ .................... A61M 31/00; A61M 7/00
[52] U.S. Cl. .................................. 424/15; 424/22
[58] Field of Search ............................ 424/15, 22

[56] References Cited

U.S. PATENT DOCUMENTS

| | | | |
|---|---|---|---|
| 3,916,899 | 11/1975 | Theeuwes et al. | 424/15 |
| 4,210,139 | 7/1980 | Higuchi | 128/260 |
| 4,265,874 | 5/1981 | Bonsen et al. | 424/15 |
| 4,327,725 | 5/1982 | Cortese et al. | 424/19 |
| 4,449,983 | 5/1984 | Cortese et al. | 424/18 |

Primary Examiner—Ronald W. Griffin
Attorney, Agent, or Firm—Paul L. Sabatine; Edward L. Mandell; Steven F. Stone

[57] ABSTRACT

An osmotic dispensing device is disclosed for delivering a medicine to a biological environment of use. The device comprises a semipermeable wall surrounding a compartment with an osmotic passageway in the semipermeable wall connecting the outside of the device with the compartment. The compartment houses a medicine releasable carrier by a means for increasing in size for delivering the beneficial medicine from the device over time.

22 Claims, 3 Drawing Figures

4,624,847

DRUG DELIVERY DEVICE FOR PROGRAMMED DELIVERY OF BENEFICIAL DRUG

FIELD OF THE INVENTION

The present invention pertains to both a novel and useful device for dispensing a beneficial drug composition at a programmed rate to a biological environment of use. More particularly, this invention concerns a beneficial drug composition that surrounds and is releasably carried by means for increasing in size for delivering the beneficial drug composition from the device over time.

BACKGROUND OF THE INVENTION

Since the beginning of antiquity, both pharmacy and medicine have long sought a delivery system for the controlled, programmed administration of a beneficial drug composition to a biological environment of use. The first recorded mention of a delivery system, a drug form, is in the Eber Papyrus written about 1552 B.C. The Eber Papyrus mentions dosage forms such as anal suppositories, vaginal pessaries, ointments, oral pill formulations, and other dosage preparations. About 2500 years passed without any advance in dosage form development, until the Arab physician Rhazes, 826–925 A.D., invented the coated pill for oral use. A century later the Persian Avicenna, 980–1037 A.D., coated pills with gold or silver for increasing patient acceptance and for enhancing the effectiveness of the drug. Also around this time the first tablet was described in an Arabian manuscripts written by Al-Zahrawi, 936–1009 A.D. The manuscript described a tablet formed from the hollow impression in two matched-facing tablet molds. Pharmacy and medicine waited about 800 years for the next innovation in dosage forms, when in 1883 Mothes invented the capsule for administering drug. Fifty-five years later Lipowski introduced a convenience dosage form to pharmacy and medicine by eliminating the necessity for taking an oral dosage form several times during the day. The dosage form invented by Lipowski in 1938 comprised a number of small beads containing a dose of drug with several thicknesses of coating designed for the slow and constant supply of drug. Eighteen years passed before Blythe introduced a tiny-timed pill dosage form similar to Lipowski's. This introduction established in pharmacy and medicine a permanent position for prolonged action, timed release dosage forms.

The next quantum and profound leap in dosage forms came in 1972 with the invention of the osmotic device by inventors Theeuwes and Higuchi. This unique delivery device is manufactured in one embodiment for oral use. In this embodiment it embraces the appearance of a tablet with a drug delivery osmotic passageway. It is the first oral dosage form that delivers throughout the entire gastrointestinal tract a known amount of drug per unit time of a dosage-controlled rate of delivery. A further pioneer advancement was presented six years later to the dispensing art by inventor Theeuwes. In this advancement, the delivery kinetics of the device was enhanced for delivering drugs with degrees of solubility in aqueous fluids that are difficult to deliver, such as very soluble or insoluble in the fluid, by manufacturing the device with an agent compartment and an osmagent compartment separated by a film, which film is movable from a rested to an expanded state. The device delivers agent by fluid being imbibed through the wall into the osmagent compartment producing a solution that causes the compartment to increase in volume and act as a driving force that is applied against the film. This force urges the film to expand against the agent compartment and correspondingly diminish the volume of this compartment, whereby agent is dispensed through the osmotic passgeway from the device. A more recent advancement in oral dosage forms was provided by Cortese and Theeuwes, who use a layer of a hydrogel for urging a layer of a beneficial drug from an osmotically operated delivery device. The device delivered the layer of drug by the hydrogel expanding and urging the beneficial drug through an osmotically calibrated passageway from the device.

While these prior art devices operate successfully for their intended use, and while they can deliver numerous difficult to deliver drugs, their use can be limited because of their structure or because of the manufacturing steps needed for fabricating a movable film or for fabricating a layer arrangement in the device. It will be appreciated by those versed in the dispensing art, that if a dispensing device can be provided without the movable film or the layer arrangement, and can be manufactured free of the tribulations known to the prior art, such a device would have a positive and practical value and represent also an advancement in the delivery art.

OBJECT OF THE INVENTION

Accordingly, it is an immediate object of this invention to provide a delivery device for the controlled delivery of a beneficial drug to an environment of use, and which device represents a further improvement and advancement in the delivery arts.

Another object of this invention is to provide a dispensing device that is useful for delivering a beneficial agent formulation that is difficult to deliver and now can be delivered by the dispensing device of this invention at meaningful rates.

Another object of this invention is to provide a dispensing device comprising a compartment containing a beneficial agent composition that substantially surrounds means for increasing in size for delivering the beneficial agent at a controlled rate from the dispensing device.

Another object of this invention is to provide a dispensing device having a compartment comprising a beneficial agent that can be from insoluble to very insoluble in an aqueous fluid, and surrounds a core comprising a drug releasing expandable hydrogel that operates to increase in size and occupy the compartment, thereby delivering the beneficial agent from the device at a controlled rate over time.

Another object of the invention is to provide a dispensing device comprising a compartment housing a beneficial medicine composition releasably coated onto a hydrogel expandable member that can generate a hydrodynamic force and expands in all directions in the compartment for dispensing the beneficial medicine through at least one osmotic passageway from the device.

Another object of the invention is to provide a dispensing device comprising a compartment containing a beneficial drug composition compressed around an expandable driving member formed of a hydrogel, which hydrogel can continuously increase in volume and correspondingly continuously occupy more of the volume of the compartment, thereby substantially maintaining a major amount of the beneficial drug present in a saturated phase throughout its release through the osmotic passageway from the device.

Another object of the invention is to provide an osmotic therapeutic device that can administer to a warm-blooded host a complete pharmaceutical regimen comprising very soluble or poorly soluble agents, at a controlled and continuous rate for a particular time period, the use of which requires intervention only for initiation and possible termination of the regimen.

Other objects, features, aspects and advantages of the invention will be more apparent to those versed in the dispensing art from the following detailed specification taken in conjunction with the drawing figures and the accompanying claims.

BRIEF DESCRIPTION OF THE DRAWINGS

In the drawings, which are not drawn to scale but are set forth to illustrate various embodiments of the invention, the drawing figures are as follows.

In the drawings and in the specification like parts in related figures are identified by like numbers. The terms appearing earlier in the specification and in the description of the drawing figures, as well as embodiments thereof, are further detailed elsewhere in the disclosure.

DETAILED DESCRIPTION OF THE DRAWINGS

Figure 1:
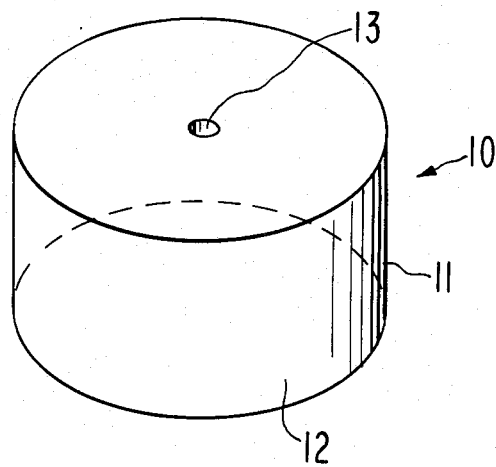
FIG. 1 is a view of a dispensing device designed and manufactured as an oral dosage form for delivering a beneficial medicine formulation to an enviroment of use, such as the gastrointestinal tract of an animal.
Figure 2:
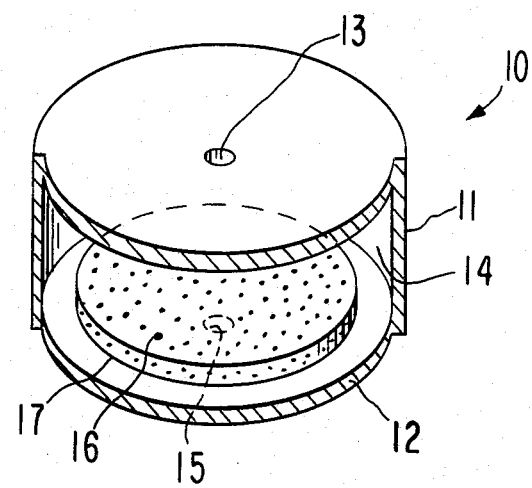
FIG. 2 is an opened view of the device of FIG. 1, illustrating the internal structure of the dispensing device.
Figure 3:
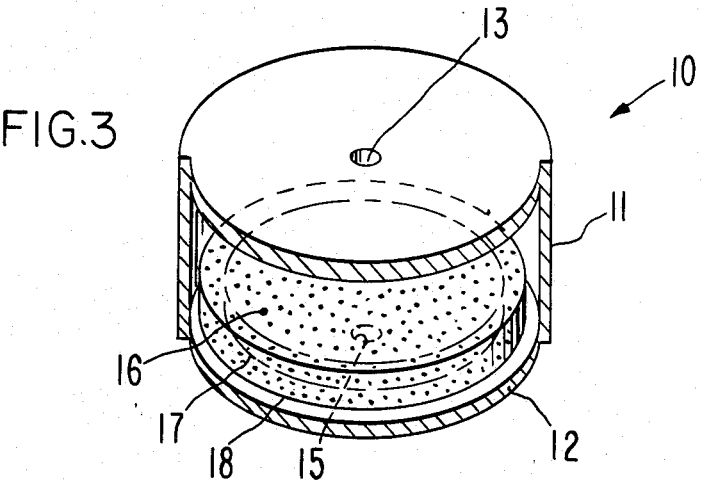
FIG. 3 is an opened view of the dispensing device of FIGS. 1 and 2 depicting the operative mode and manner of the device.

Turning now to the drawing figures in detail, which are an example of an osmotic dispensing device provided by the invention, and which drawing figures are not to be construed as limiting, one example of an osmotic dispensing device is seen in FIGS. 1, 2 and 3. In FIG. 1, osmotic device 10 is seen comprising a body member 11 comprising a wall 12 that surrounds and forms an internal compartment not seen in FIG. 1. Osmotic dispensing device 10 is provided with an osmotic passageway in wall 12, which osmotic passageway connects the exterior of osmotic device 10 with the interior of device 10.

In FIG. 2, osmotic dispensing device 10 is seen in opened section. In FIG. 2, osmotic device 10 comprise body 11, wall 12, osmotic passageway 13 and internal compartment 14. In FIG. 2, osmotic dispensing device 10 comprises a second osmotic passageway 15 that also connects the exterior of device 10 with interior compartment 14. Wall 12 of device 10 is formed of a nontoxic polymeric composition that is totally, or in at least a part, permeable to the passage of an external fluid, and it is substantially impermeable to the passage of a beneficial drug formulation. The polymeric composition forming wall 12 is inert and it maintains its physical and chemical integrity during the dispensing life of osmotic device 10.

Internal compartment 14 houses a beneficial drug composition 16, identified by dots, which drug composition 16 is releasably supported by an expandable means 17. Beneficial drug composition 17 comprises a drug that can be form insoluble to very soluble in an aqueous fluid, and it is mixed with an osmopolymer for coating or compressing it around means 17. Beneficial drug composition 16 in an another embodiment comprises a drug, an osmopolymer and an osmagent. The osmopolymer suitable for this purpose is hydrophilic water soluble, noncross-linked or lightly cross-linked, and it possesses the properties for blending with a drug that can be compressed or coated around means 17. The osmopolymer exhibits an osmotic pressure gradient across a semipermeable wall against an external fluid present in the environment of use and it imbibes fluid through semipermeable wall into compartment 14.

Expandable means 17 is formed of a hydrogel that is an osmopolymer. The osmopolymer suitable for this purpose possesses the property of serving as a releasable carrier for drug composition 16. Composition 16 can be coated or compressed onto means 17, and it substantially surrounds means 17. The osmopolymer used for forming means 17 exhibits an osmotic pressure gradient across wall 12, it imbibes fluid, it is noncross-linked or lightly cross-linked, and it expands or swells in the presence of fluid that enters compartment 14. The osmopolymer forming means 17 in a presently preferred embodiment is different than the osmopolymer forming drug composition 16; and in another embodiment it can possess the same structure with the proviso that it has a greater molecular weight. The osmopolymer forming means 17 in another embodiment can be mixed with an osmagent, which osmagent is soluble in the external fluid and exhibits an osmotic pressure gradient across wall 12 against an external fluid.

Device 10, in operation in a fluid biological environment of use, delivers drug by imbibing exterior fluid through semipermeable wall 12 into compartment 14, in a continuous tendency towards osmotic equilibrium. The imbibition occurs at a rate determined by the permeability of semipermeable wall 12 and the osmotic pressure gradient across wall 12. The imbibed fluid continuously forms (1) a solution or suspension containing beneficial drug, (2) a solution or suspension containing beneficial drug and the osmopolymer present in composition 16, or (3) a solution or suspension containing the beneficial drug, the osmopolymer and the osmagent present in composition 16. In any instance, beneficial drug is delivered through osmotic passageway 13 and from device 10.

Concurrent with the above operation, means 17 imbibes fluid into compartment 14 and absorbs fluid and swells or expands to some equilibrium state. At equilibrium, the osmotic pressure of the hydrogel means approximately equals the swelling pressure of the hydrogel means, and this osmotic pressure of the hydrogel network is the driving force of the swelling, expanding means 17. Hydrogel means 17 by imbibing fluid continuously increases in volume, as seen in FIG. 3, means 17 expands from a rested state 17 to an expanded state 18, thereby occupying more volume of compartment 14 and urging beneficial drug 16 through osmotic passageways 13 and 15. The combined operations of the formation of the deliverable fluid drug formulation, the swelling and expansion of hydrogel means 17, along with the simultaneous take-up of space in compartment 14, assures the delivery of beneficial drug 14 at a controlled rate over time.

FIGS. 1 through 3 depict one presently preferred embodiment of dispensing device 10. In this embodiment device 10 is made for oral use, that is, for releasing a locally acting medicine, or a systemically acting medicine in the gastrointestinal tract. The oral system can have various shapes and sizes. In one design, device 10 can be curved, such as round, with a diameter is ⅛ inch to 9/16 inch, or it can be shaped like a capsule having a range of sizes from triple zero to zero, and from 1 to 8.

While FIGS. 1 through 3 illustrate one dispensing device that can be made according to the invention, it is to be understood device 10 can take a wide variety of shapes, sizes and forms for delivering a beneficial medicine to the environment of use. For example, the osmotic devices include buccal, implant, artificial gland, cervical, intrauterine, nose and the like osmotic devices. In these forms device 10 can be adapted for administering a beneficial medicine to numerous animals, warm-blooded mammals, humans, avians, farm animals and reptiles.

DETAILED DESCRIPTION OF THE INVENTION

In accordance with the practice of the invention, it now has been found that delivery device 10 can be manufactured with a wall 12 formed of a material that does not adversely affect beneficial agent 16, which includes drug, and it does not adversely affect an osmopolymer, an osmagent, an animal, or a host. Wall 12 is formed of in at least a part of polymeric composition permeable to the passage of an external aqueous-type fluid such as water and biological fluids, while remaining essentially impermeable to the passage of beneficial drug 16, osmagent, osmopolymer and the like. The selectively semipermeable materials forming wall 12 are insoluble in fluids, and they are non-erodible, hence they maintain their physical and chemical integrity during the operation of the device in the environment of use.

Typical materials for forming wall 12 include semipermeable polymers known to the art as osmosis and reverse osmosis membranes. These include cellulose ester, cellulose ether, cellulose ester-ether, cellulose acylate, cellulose diacylate, cellulose triacylate, cellulose acetate, cellulose diacetate, cellulose triacetate, agar acetate, amylose triacetate, beta glucan acetate, cellulose acetaldehyde dimethyl acetate, cellulose acetate ethyl carbamate, cellulose acetate methyl carbamate, cellulose acetate succinate, cellulose acetate dimethylaminoacetate, cellulose acetate ethyl carbamate, cellulose acetate chloroacetate, cellulose dipalmate, cellulose dioctanoate, cellulose dicaprylate, cellulose dipentanlate, cellulose acetate valerate, cellulose acetate succinate, cellulose propionate succinate, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; lightly cross-linked semipermeable polystyrene derivative, cross-linked semipermeable poly(sodium styrene sulfonate), semipermeable poly(-vinylbenzyltri-methylammonium chloride), cellulose acetate having a degree of substitution up to 1 and an acetyl content up to 21%, cellulose diacetate having a degree of substitution of 1 and 2 and an acetyl content of 21 to 35%, cellulose triacetate having a degree of substitution of 2 to 3 and an acetyl content of 35 to 44.8%, as disclosed in U.S. Pat. No. 4,160,020. Generally, semipermeable materials used for forming wall 12 will have a fluid permeability of $10^{-5}$ to $10^{-1}$ (cc mil/cm$^2$ hr/atm) expressed per atmosphere of hydrostatic or osmotic pressure difference across semipermeable wall 12 can be used for the intended purpose.

When wall 12 is formed in at least a part of a semipermeable polymeric composition, the remainder of wall 12 is formed of a polymeric composition that is impermeable to the passage of fluid drug and the like. Representative fluid and drug impermeable polymers include impervious polytetrafluoroethylene, impermeable polyamides, impermeable polyaminotriazoles, impermeable polynonamethyleneurea, polysulfones, and the like.

The osmopolymers suitable for forming beneficial drug composition 16 and also suitable for forming the means 17, are osmopolymers that exhibit fluid imbibition properties. The osmopolymers are swellable, hydrophilic polymers which interact with water and aqueous biological fluids and swell, or expand to an equilibrium state. The osmopolymers exhibit the ability to swell in water and retain a significant portion of the imbibed water within the polymer structure. The osmopolymers swell or expand to a very high degree, usually exhibiting a 2 to 50 fold volume increase. The swellable, hydrophilic polymers are in one presently preferred embodiment lightly cross-linked, such crosslinks being formed by covalent or ionic bonds. The osmopolymers can be of plant, animal or synthetic origin. The osmopolymers are hydrophilic polymers. Hydrophilic polymers suitable for the present purpose include poly(hydroxyalkyl methacrylate) having a molecular weight of from 30,000 to 5,000,000; poly(vinylpyrrolidone) having a molecular weight of from 10,000 to 360,000; anionic and cationic hydrogels; polyelectrolyte complexes; poly(vinyl alcohol) having a low acetate residual, cross-linked with flyoxal, formaldehyde, or glutaraldehyde and having a degree of polymerization from 200 to 30,000; a mixture of methyl cellulose, cross-linked agar and carboxymethyl cellulose; a water-insoluble, water-swellable copolymer produced by forming a dispersion of finely divided copolymer of maleic anhydride with styrene, ethylene, propylene, butylene or isobutylene cross-linked with from 0.001 to about 0.5 moles of polyunsaturated cross-linked agent per mole of maleic anhydride in the copolymer; water-swellable polymers of N-vinyl lactams, and the like.

Other osmopolymers include polymeric hydrogels such as Carbopol ® acidic carboxy polymers having a molecular weight of 450,000 to 4,000,000; Cyanamer ® polyacrylamides; cross-linked water-swellable indene-maleic anhydride polymers; Good-rite ® polyacrylic acid having a molecular weight of 80,000 to 200,000; Polyox ® polyethylene oxide polymers having a molecular weight of 100,000 to 5,000,000; starch graft copolymers; Aqua-Keeps ® acrylate polymer; diester cross-linked polyglucan, and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels; and in *Handbook of Common Polymers*, by Scott and Roff, published by the Chemical Rubber Company, Cleveland, OH. The amount of osmopolymer contained in beneficial drug composition 16 generally is from about 0.01 to 99% of composition 16. The amount of osmopolymer comprising means 17 generally is 100%, or less if an osmagent is dispersed throughout means 17. In a presently preferred emodiment, the molecular weight of the osmopolymer comprising means 17 is larger, than the molecular weight of the osmopolymer present in beneficial drug composition 16.

An osmopolymer can be selected for forming beneficial drug composition 16 or means 17 by fluid imbibition determinations. The imbibition determination indicates the imbibition value of an osmopolymer, which value depicts the rate of fluid uptake over time, and correspondingly the operative properties of an osmopolymer in a dispensing device. The osmopolymer fluid imbibition determination for a chosen polymer can be made by following the procedure described below. A ½ inch round disc, fitted with a ½ inch diameter stainless steel plug is charged with a known quantity of polymer with the plugs extending out either end. The plugs and the die are placed in a Carver press with plates between 200° F. and 300° F. A pressure of 10,000 to 15,000 psi was applied to the plugs. After 10 to 20 minutes of heat and pressure the electrical heating to the plates was turned off, and tap water circulated through the plates. The resulting ½ inch discs were placed in an air suspension coater charged with 1.8 kg saccharide cores and coated with cellulose acetate having an acetyl content of 39.8% dissolved in 94:6 w/w, $CH_2Cl_2/CH_3OH$, to yield a 3% wt:wt solution. The coated systems were dried overnight at 50° C. The coated discs were immersed in water at 37° C. and periodically removed for a gravimetric determination of water imbibed. The initial imbibition pressure was calculated by using the water transmission constant for the cellulose acetate, after normalizing imbibition values for membrane surface area and thickness. The polymer used in this determination was the sodium derivative of Carbopol-934 ® polymer, prepared according to the procedure of *B. F. Goodrich Service Bulletin GC-36*, "Carbopol ® Water-Soluble Resins", p 5, published by B. F. Goodrich, Akron, OH.

The cumulative weight gain values, y as a function of time, t, for the water soluble polymer disc coated with the cellulose acetate were used to determine the equation of the line $y = c + bt + at^2$ passing through those points by a least square fitting technique.

The weight gain for the NaCarbopol-934 ® is given by equation as follows: Weight gain equals $0.359 + 0.665t - 0.00106t^2$ wherein t is elapsed time in minutes. The rate of water flux at any time will be equal to the slope of the line that is given by the following equation:

$$dy/dt = d(0.359 + 0.665t - 0.00106t^2)/dt$$
$$dy/dt = 0.665 - 0.002t$$

To determine the initial rate of water flux the derivative is evaluated at $t=0$, and $dy/dt = 0.665$ μl/min., which is equal to the coefficient b. Then, normalizing the imbibition rate of time, membrane surface area and thickness, the membrane permeability constant to water, $K\pi$, may be determined according to the following equation:

$$K\pi = 0.665 \, \mu l/min \times (60 \, min/hr) \times (1 \, ml/1000 \, \mu l)(0.008 \, cm/2.86 \, cm^2)$$

with $K\pi = 1.13 \times 10^{-4}$ cm²/hr. The $\pi$ value for NaCl was determined with a Hewlett-Packard vapor pressure osmometer to be 345 atm±10% and, the K value for cellulose acetate used in this experiment calculated from NaCl imbibition values to be $2.1 \times 10^{-7}$ cm²/hr.atm. Substituting into the calculated $K\pi$ expression $(2.1 \times 10^{-7}/cm^2/hr.atm)(\pi) = 1.13 \times 10^{-4}$ cm²/hr. $\pi = 600$ atm at $t=0$. As a method for evaluating the efficiency of a polymer with respect to duration of zero-order driving force, the percent of water uptake was selected before the water flux values decreased to 90% of their initial values. The value of the initial slope for the equation of a straight line emanating from the percent weight gained axis will be equal to the initial value of dy/dt evaluated at $t=0$, with the y intercept c defining the linear swelling time, with $(dy/dt)0 = 0.665$ and the y intercept $= 0.359$, which yields $y = 0.665t + 0.359$. In order to determine when the value of the cumulative water uptake is 90% below the initial rate, the following expression is solved for t:

$$0.9 = (at^2 + bt + c)/(bt + c) = (\Delta wt/wt)0.9( -0.00106t^2 + 0.665t + 0.359)/(0.665t + 0.359) = 0.9,$$

and solving for t $$-0.00106t^2 + 0.0065t + 0.0359 = 0 \, t = (-0.0065 \pm [(0.0665)^2 - 4(-0.00106)(0.0359)]^{\frac{1}{2}}/2(-0.00106)$$

$t = 62$ min and the weight gain is $-0.00106(62)^2 + (0.665)(\beta) + 0.359 = 38$ μl with the initial sample weight $= 100$ mg. thus ($\Delta wt/wt$). $9 \times 100 = 38\%$ Other methods available for studying the hydrogel solution interface include rheologic analysis, viscometric analysis, elipsometry, contact angle measurements, electokinetic determinations, infrared spectroscopy, optical microscopy, interface morphology and microscopic examination of an operative device.

The osmagent present in device 10 is present in beneficial drug composition 16 or present in means 17. The osmagent present in osmotic device 10, when used according to the mode of the invention, are osmotically effective compounds soluble in fluid that enter the device and exhibit an osmotic pressure gradient across a semipermeable wall against the exterior fluid. Osmotically effective osmagents useful for the present purpose include magnesium sulfate, magnesium chloride, sodium chloride, lithium chloride, potassium sulfate, sodium carbonate, sodium sulfite, lithium sulfate, potassium chloride, sodium sulfate, d-mannitol, urea inositol, raffinose, glycose, mixtures thereof, and the like. The osmagent is usually present in an excess amount, and it can be in any physical forms, such as particle, powder, granule, and the like. The osmotic pressure in atmospheres, atm, of the osmagents suitable for the invention will be greater than zero atm, generally from zero atm up to 500 atm, or higher. The amount of osmagent blended homogeneously or heterogeneously in beneficial composition 16 generally is, for the purpose of this invention, from 0.01 to 50%, with the total weight of all ingredients comprising composition 16 being 100%. The amount of osmagent blended homogeneously or heterogeneously with the osmopolymer comprising means 17 is generally from 0.01 to 60% with the weight percent of the ingredients comprising means 17 being 100%. The osmotically effective compounds are known to the art in U.S. Pat. Nos. 4,177,256 and 4,449,983.

The expression beneficial drug composition 16 and beneficial medicine formulation as used herein denotes a beneficial drug neat, and a composition comprising a beneficial drug and an osmopolymer and, optionally, an osmagent. In the specification and the accompanying claims, the term medicine and drug are used as equivalents, and the term drug includes any physiologically or pharmacologically active substance that produces a local or systemic effect in animals, including warm-blooded mammals; human and primates; fishes; reptiles; farm, sport and zoo animals. The term 'physiologically' as used herein denotes the administration of a drug to produce normal levels and functions. The term 'pharmacologically' denotes variations in response to amount of drug administered to the host. *Stedman's Medical Dictionary*, 1966, published by Williams and Wilkins, Baltimore, MD. The active drug that can be delivered includes inorganic and organic drugs without limitations, those drugs that act on the central nervous system, depressants, hypnotics, sedatives, psychic energizers, tranquilizers, anticonvulsants, muscle relaxants, anti-parkinson agents, analgesics, anti-inflammatory, local anesthetics, muscle contractants, anti-microbials, anti-malarials, hormonal agents, contraceptives, sympathomimetics, diuretics, anti-parasitics, neoplastics, hypoglycemics, ophthalmics, electrolytes, diagnostic agents and cardiovascular drugs. The amount of medicine carried, coated or compressed onto and around core means 17 generally is from 0.1 mg to 425 mg of medicine, or 0.1 to 80% of a beneficial composition on a total weight basis of 100% for all ingredients. Of course, lower and higher amounts in those embodiments are within the scope of the invention.

Exemplary drugs that can be carried on the core means 17 and delivered by the osmotic device of this invention include prochlorperazine edisylate, prochlorperazine maleate, prazosin hydrochloride, clonidine hydrochloride, hydrallazine hydrochloride, dextromethorpan hydrobromine, dextroamphetamine phosphate, diethylpropionm hydrochloride, isoxsuprine hydrochloride, ambenonium chloride, phenoxybenzamine hydrochloride, phentolamine hydrochloride, guanethidine sulfate, clidinium bromide, glycopyrrolate, homatropine methylbromide, hyoscyamine hydrobromide, mepenzolate bromide, methscopolamine bromide, balofen, and the like. These drugs and their daily dose are known to the art in *Pharmaceutical Sciences*, by Remington, 16th Ed., 1980, published by Mack Publishing Company, Easton, PA.

The medicine can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate and salicylate. For acid medicine, salts of metals, amines or organic cations, for example, quaternary ammonium can be used. Derivatives of medicine such as esters, ethers and amides can be used. Also, a medicine that is water insoluble can be used in a form that is a water soluble derivative thereof to serve as a solute and, on its release from the devices, it is converted by enzymes, hydrolyzed by body pH or other metabolic process to the original biologically active form.

The solubility of a medicine in the fluid that enters the compartment can be determined by known techniques. One method consists of preparing a saturated solution comprising the fluid plus the medicine as ascertained by analyzing the amount of medicine present in a definite quantity of the fluids. A simple apparatus for this purpose consists of a test tube of medium size fastened upright in a water bath maintained at constant temperature and pressure, in which the fluid and medicine are placed and stirred by a rotating glass spiral. After a given period of stirring, a weight of the fluid is analyzed and the stirring continued an additional period of time. If the analysis shows no increase of dissolved medicine after successive periods of stirring, in the presence of excess solid medicine in the fluid, the solution is saturated and the results are taken as the solubility of the produce in the fluid. If the medicine is soluble, an added osmotically effective compound optionally may not be needed. If the medicine has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin*, No. 67 of the Hygenic Laboratory; Encyclopedia of Science and Technology, Vol. 12, pp 542–556, 1971, published by McGraw-Hill, Inc.; and, *Encyclopedia Dictionary of Physics*, Vol. 6, pp 547–557, 1962, published by Pergammon Press, Inc.

The expressions "passageway", "passageway communicating with" and "means for releasing", as used herein comprises those means and methods suitable for delivering the beneficial drug composition according to the osmotic properties of the components present in compartment 14 and the hydrogel means present in compartment 14. The expressions include "passageway", "aperature", "orifice", "bore", "pore", "porous element" through which the beneficial agent can migrate, "hollow fiber", "capillary tube", and the like. The expressions also include materials that erode in the environment of use to produce a passageway in the device. Representative matrials suitable for forming a passageway include an erodible poly(glycolic) and poly(lactic) acids in the wall, gelatinous filaments, poly(vinyl alcohol), and the like. The passageway also can be formed by leaching a material such as sorbitol from the wall. The passageways can have any shape. For example, round, triangular, square, elliptical, irregular, and the like. Also, the device can be constructed with one or more passageways. In an embodiment when the device is fabricated with more than one passageway they can be construed as the functional equivalent in an operative embodiment of a single osmotic passageway.

The passageway in one embodiment includes a passageway formed by mechanical drilling or laser drilling through the wall. Generally for the purpose of this invention, the passageway will have a maximum cross-sectional area, A, defined by equation A:

$$L/F \times Qv/t \times 1/DS \text{ TM (A)}$$

wherein L is the length of the passageway, (Qv/t) is the mass delivery rate of the agent D released per unit of time, D is the diffusion coefficient of the medicine in the release solution, S is the solubility of the medicine in the fluid and F has a value of approximately 2 to 1000, said osmotic passageway having a minimum area, $A_s$, defined by equation B.

$$\left[ \frac{Lv}{t} \times 8 \times \frac{\pi \eta}{\Delta P} \right]^{\frac{1}{2}} \quad \text{(B)}$$

wherein L is the length of the passageway, v/t is the volume of the medicine released per unit of time, $\pi$ is 3.14, $\eta$ is the viscosity of the solution being released, and $\Delta P$ is the hydrostatic pressure difference between the inside and the outside of the compartment and having a value up to 20 atm. The passageways are known to the prior art in U.S. Pat. Nos. 3,845,770; 3,916,899;

4,016,880; 4,200,098; 4,235,236, and 4,320,759. Laser drilling machines equipped with photo wave length detecting systems for orienting a device are known in U.S. Pat. No. 4,063,064 and in U.S. Pat. No. 4,088,864.

The osmotic device of the invention is manufactured using standard machines. For example, in one embodiment a plurality of core forming particles are compressed under a pressure head up to 50 tons into a solid, compacted mass and then coated with a medicine. In another embodiment, a polymer is cut into a shape corresponding to the shape of a compartment of an osmotic device and then the shaped and sized core member is coated with a medicine formulation. In another embodiment a medicine and an osmagent, and optionally other ingredients that may be housed in the compartment of an osmotic device, are blended to form a homogeneous composition and the pressed onto a solid core possessing dimensions that correspond to the internal dimensions of the area to be occupied in the compartment. The various ingredients can be mixed with a solvent by ballmilling, calendering, stirring or rollmilling, and then pressed onto the preselected shaped core. In another manufacture the medicine can be coated by dipping or air suspension coating onto the core member. The semipermeable wall can be applied around the medicine core by molding, spraying or dipping the medicine coated, pressed shapes into a wall forming material. Another presently preferred technique that can be used for applying the wall is the air suspension procedure. This procedure consists in suspending and tumbling the medicine coated core in a current of air and a wall forming composition until the wall is applied to the composite. The air suspension procedure is described in U.S. Pat. No. 2,779,241. *J. Am. Pharm. Assoc.*, Vol. 48, pp 451–459, 1979, and ibid., Vol. 49, pp. 82–84, 1960. Other standard manufacturing procedures are described in *Modern Plastics Encyclopedia*, Vol. 46, pp 62–70, 1969; and in *Pharmaceutical Sciences*, by Remington, 14th, Ed., pp 1626–1678, published by Mack Publishing Company, Easton, PA.

Exemplary solvents suitable for manufacturing the wall and the core include inorganic and organic solvents that do not adversely harm the wall and the core forming material, and the final device. The solvents broadly include members selected from the group consisting of aqueous solvents, alcohols, ketones, esters, ethers, aliphatic hydrocarbons, halogenated solvents, cycloaliphatic aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butylacetate, methyl isobutyl ketone, methyl propyl ketone, n-hexane, n-heptane, ethylene glycol monoethyl ether, ethelene glycol monoethyl acetate, methylene dichloride, ethylene dichloride, propylene dichloride, carbon tetrachloride, nitroethane, nitropropane, tetra-chloroethane, ethyl ether, isopropyl ether, cyclohexane, cyclo-octane, benzene toluene, naptha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol, and the like.

The following example illustrates means and methods for carrying out the present invention. The example is merely illustrative and it should not be considered as limiting the scope of the invention, as this example and other equivalents thereof will become more apparent to those versed in the dispensing art in the light of the present disclosure, the drawings and the accompanying claims.

EXAMPLE 1

A dispensing device for the controlled delivery of the beneficial drug haloperidol is manufactured as follows: First, 646 grams of Polyox ® coagulant, a poly(ethylene oxide) having a molecular weight of about 5,000,000 is blended wih 293 grams of sodium chloride and 50 grams of hydroxypropyl methylcellulose in a commercial mixer for 20 minutes to produce a uniform blend. Next, the blend is dampened with 910 millileters of absolute ethanol with constant stirring over a period of 15 to 20 minutes to produce granules. Next, the granules are dried at 22° C. in a forced air oven for 24 hours and then passed through a 20 mesh screen. The granules are then pressed in a 5/16 inch tablet machine under a pressure head of 3 ton to yield active expanding inner cores suitable for use as the driving means of the device. The cores weigh about 250 mgs.

Next, a beneficial drug composition is prepared by blending 5 grams of haloperidol, 80 grams of Polyox ® N-10 poly(ethylene oxide) having a molecular weight of about 100,000, and 15 grams of hydroxypropylmethylcellulose in a commercial mixer in the presence of a solvent consisting of 1170 milliliters of methylene chloride and 480 milliliters of methanol (80:20 wt:wt). The ingredients are blended for 25 to 30 minutes. Then, the beneficial drug composition is coated around the core using an Aeromatic ® air-suspension coater, until each core is coated with a 20 mg coat of the beneficial drug composition.

Then, a rate controlling wall is applied around the beneficial drug composition cores. The rate controlling semipermeable wall is prepared as follows: First, 90 grams of cellulose acetate having an acetyl content of 39.8% and 10 grams of poly(ethylene glycol) having a molecular weight of 3350 are dissolved in a methylene chloride:methanol solvent (90:10 wt:wt) to obtain 4% solids. The beneficial haloperidol composition coated cores are placed in an air suspension machine, an Aeromatic ® air suspension coater, the solvent is fed thereto, and the haloperidol coated cores surrounded with a semipermeable wall of cellulose acetate. The semipermeable wall weighs about 5 mg. The system then is dried for 24 hours at 50° C. in a forced air oven to evaporate the solvent. Finally, a passageway is laser drilled on both sides to yield the dispensing device. The device delivers haloperidol for 10 hours in artificial gastric and artificial intestinal juice.

EXAMPLE 2

The active-expandable inner means prepared in Example 1 is used in this example. The beneficial drug formulation in this example is prepared from 10 grams of midazolam, 80 grams of Polyox ® N-10 poly(ethylene oxide) and 10 grams of hydroxypropyl methylcellulose having a viscosity of 6 centipoises in a 2% aqueous solution at 20° C., dissolved in 1200 milliliters of methylene chloride and 500 milliliters of methanol. The inner means is surrounded with a layer of beneficial drug formulation containing 5 mg of midazolam.

Finally, a rate controlling semipermeable wall is placed around the medicine coated core. This procedure consists essentially of first dissolving cellulose acetate having an acetyl content of 45%, cellulose acetate having an acetyl content of 45%, and hydroxypropyl methylcellulose 10%, in 1900 grams of methylene chloride:methanol solvent (90:10 wt:wt). The medicine coated cores are surrounded with a cellulose acetate wall in an air suspension machine with a semipermeable wall that weighs about 30 mg. The dispensing devices next are dried in a forced air oven for 48 hours at 50° C., to free the devices of solvent. Then, a passageway is drilled through the semipermeable wall, device turned over and a passageway drilled through the opposite wall. The device delivers the beneficial drug midazolam for about 8 hours in artificial gastric and artificial intestinal fluids. Artificial gastric fluid and artificial intestinal fluid are prepared according to the procedure in *The United States Pharmacopeia*, 20th Revision, p 1105, published in 1980 by United States Pharmacopeial Convention, Inc., Rockville, MD.

EXAMPLE 3

A controlled delivery system for the delivery of the beneficial drug prazosin is prepared as follows: First, 94 milligrams of Carbopol ® 934-P, (a polymer of acrylic acid lightly cross-linked with a polyallyl ether of sucrose having an average of 5.8 allyl groups per each sucrose molecule as disclosed in U.S. Pat. Nos. 2,909,462; 3,033,754; 3,330,729; 3,458,622; 3,459,850; 4,170,760; and 4,248,857), 4 milligrams of hydroxypropyl methylcellulose having a viscosity of 5 centipoises in 2% aqueous solution at 20° C., and 2 milligrams of magnesium stearate are blended into a homogeneous mass by blending the Carbopol ® polymer and the hydroxypropyl methylcellulose by roller compacting and milling said compaction in a planetary mixer to 16-mesh particle size. Then the granulation is lubricated with the magnesium stearate in a V-blender for 10 to 15 minutes. The resultant granulation is then tableted into $\frac{1}{4}$ inch (7 mm) cores.

Next, the expandable inner cores are coated with a solution comprising 74% Polyox ® N-10 (a poly(ethylene oxide) with a molecular weight of about 100,000), 10% hydroxypropyl methylcellulose and 16% prazosin hydrochloride in a methylene chloride/ethanol (90:10 wt:wt) solvent, containing 3% (wt:wt) solids. The coating is carried out in an air suspension apparatus. The beneficial drug layer that surrounds the core weighs 12 milligrams. Next, the drug coated cores are surrounded with a semipermeable rate-controlling membrane consisting essentially of 90% cellulose acetate having an acetyl content of 39.8% and 10% hydroxypropyl methylcellulose. The coating solvent is 91% (wt:wt) methylene chloride and 9% (wt:wt) ethanol. The coating solids are 3.5%. The wall is applied in an air suspension coater, and the approximate average weight of the wall is 30 milligrams. A 20 ml (0.512 mm) passageway is laser drilled into two sides of the dispensing device. The devices have an average rate of release of 0.25 mg/hr.

EXAMPLE 4

The procedure described in Example 3 is repeated in this example, with all conditions and procedures as previously described, except that the inner expandable means consist of 58% poly(ethylene oxide) having a molecular weight of about 5,000,000; 20% poly(vinyl pyrrolidone) having a molecular weight of 10,250; 10% sodium chloride and 2% stearic acid and weighs 342 mg. The compressed means have a diameter of $\frac{3}{8}$ inches (6 mm). The beneficial drug overcoat surrounding the means consists of 40% nifedipine, 15% hydroxypropyl methylcellulose, and 45% poly(ethylene oxide) having a molecular weight of 200,000. The overcoat weighs 75 mg, and the coating solvent is 90% (wt:wt) methylene chloride, 10% (wt:wt) methanol. The semipermeable wall that surrounds the beneficial drug composition coated inner means consists of 93% cellulose acetate having an acetyl content of 39.8% and 7% poly(ethylene glycol) having a molecular weight of 4000. The wall is formed by conventional pan coating. A 15 mil (0.375 mm) passageway is hand drilled into two surfaces of the dispensing device. An average rate of release of 1.6 mg/hr is obtained.

EXAMPLE 5

A delivery device for the controlled delivery of the beneficial drug atropine sulfate, an anticholinergic, is prepared as follows: First, a formulation comprising 70% atropine sulfate, 25% hydroxypropyl methylcellulose and 5% polyvinyl pyrrolidone is dissolved in an organic solvent consisting essentially of methylene chloride:methanol (60:40 wt:wt), to yield a beneficial drug composition containing 8% solids. Then, a plurality of cores, each weighing 220 mg, having a diameter of $\frac{3}{8}$ inch and made of starch graft copolymer are coated with the drug formulation in a Wurster air suspension machine. Next, the drug coated cores are surrounded with a semipermeable wall. The wall is formed from a wall-forming composition comprising cellulose acetate having an acetyl content of 36% dissolved in a solvent comprising methylene chloride:methanol (90:10 wt:wt), to obtain a wall-forming solution containing 5% solids. Each core is surrounded with the semipermeable wall forming composition until the wall weighs about 15 mg. Finally, the dispensing devices are removed from the air suspension machine and dried in a forced air over for 2 days at 50° C. Then, after cooling to room temperature, a 0.26 mm passageway is laser drilled through one surface of the device and a 0.26 mm passageway is laser drilled through a distant surface of the device for dispensing the atropine sulfate. Laser machines are commercially available from Coherent Radiation of California and Photon Sources of Michigan.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modification, changes, additions and omissions in the system illustrated and described can be made without departing from the spirit of the invention.

We claim:

1. A dispensing device for delivering a beneficial medicine formulation to an environment of use, comprising:
   (a) a wall comprising in at least a part of a semipermeable composition permeable to the passage of an exterior fluid present in the environment of use and substantially impermeable to the passage of a beneficial medicine formulation, the wall surrounding and forming;
   (b) a compartment;
   (c) means in the compartment for increasing in size from a rested state to an expanded state for occupying more volume of the compartment;
   (d) a medicine formulation in the compartment substantially coated around the means; and, (e) means in the wall connecting the exterior of the device with the compartment for delivering the medicine from the device over time.

2. The dispensing device for delivering the beneficial medicine formulation according to claim 1, wherein the beneficial medicine formulation is releasably coated around the means in the compartment.

3. The dispensing device for delivering the beneficial medicine formulation according to claim 1, wherein the means in the compartment possesses a resting shape that corresponds to the shape of the compartment.

4. The dispensing device for delivering the beneficial medicine formulation according to claim 1, wherein the means for increasing in size possesses an initial shape and size adapted for placement in the dispensing device.

5. The dispensing device for delivering the beneficial medicine formulation according to claim 1, wherein the means in the wall is a passageway.

6. The dispensing device for delivering the beneficial medicine formulation according to claim 1, wherein there is more than one means in the wall.

7. The dispensing device for delivering the beneficial medicine formulation according to claim 1, wherein the medicine formulation comprises a medicine and an osmagent.

8. The dispensing device for delivering the beneficial medicine formulation according to claim 1, wherein the medicine formulation comprises a medicine and an osmopolymer.

9. The dispensing device for delivering the beneficial medicine formulation according to claim 1, wherein the medicine formulation comprises a medicine, an osmagent and an osmopolymer.

10. The dispensing device for delivering the beneficial medicine formulation according to claim 1, wherein the environment of use is an animal and the dispensing device delivers the medicine to said animal.

11. The dispensing device for delivering the beneficial medicine formulation according to claim 1, wherein the means in the compartment is an osmopolymer.

12. The dispensing device for delivering the beneficial medicine formulation according to claim 1, wherein the means in the compartment comprises an osmopolymer and an osmagent.

13. The dispensing device for delivering the beneficial medicine formulation according to claim 1, wherein the means in the wall connecting the exterior of the device with the compartment for delivering the medicine formulation from the device over time comprises at least one pore.

14. A dispensing device for orally delivering a beneficial drug to a biological environment of use, comprising:
(a) a shaped wall comprising a semipermeable composition permeable to the passage of an exterior fluid present in the environment of use, and substantially impermeable to the passage of drug, the wall surrounding and forming:
(b) a compartment comprising a drug that surrounds and is carried by a hydrogel which hydrogel can expand from a rested to an expanded state in more than one direction in the presence of an exterior fluid that enters the compartment; and,
(c) a passageway in the wall communicating with the exterior of the device and the compartment for delivering the drug from the device at a controlled rate over time.

15. The dispensing device for orally delivering a beneficial drug according to claim 14, wherein the drug is mixed with an osmagent that is soluble in fluid that enters the compartment and exhibits an osmotic pressure gradient across the semipermeable wall against the exterior fluid.

16. The dispensing device for orally delivering a beneficial drug according to claim 14, wherein the drug is mixed with an osmopolymer that imbibes fluid that enters the compartment.

17. The dispensing device for orally delivering a beneficial drug according to claim 14, wherein the hydrogel is noncross-linked.

18. The dispensing device for orally delivering a beneficial drug according to claim 14, wherein the hydrogel is cross-linked.

19. The dispensing device for orally delivering a beneficial drug according to claim 14, wherein an osmotically effective solute is mixed with the hydrogel.

20. The dispensing device for orally delivering the beneficial drug according to claim 14, wherein the passageway in the wall communicating with the exterior of the device and the compartment for delivering the drug from the device at a controlled rate over time is a pore.

21. A method for delivering a medicine formulation to a fluid environment of use, wherein the method comprises:
(a) admitting into the fluid environment of use a dispensing device comprising:
(1) a wall comprising a semipermeable composition permeable to the passage of fluid present in the environment of use and substantially impermeable to a medicinal formulation surrounding and defining:
(2) a compartment;
(3) means in the compartment for increasing in volume and expanding outward toward the wall;
(4) a medicine formulation in the compartment surrounding said means;
(5) a first and second passageway in the wall communicating with the fluid environment and the compartment for delivering the medicine formulation from the device;
(b) imbibing fluid from the environment into the compartment to form a solution containing the medicine formulation and for sorption by the means causing it to increase in volume and expand toward the wall and urge the medicine formulation through the passageway; and,
(c) delivering the medicine formulation through the passageway from the device to the fluid environment of use.

22. The method for delivering the medicine formulation to a fluid environment of use according to claim 21, wherein the passageway in the wall comprises a pore formed by leaching sorbitol from the wall for delivering the medicine formulation through the wall from the dispensing device.

* * * * *